United States Patent [19]

Wevers

[11] 4,246,660
[45] Jan. 27, 1981

[54] ARTIFICIAL LIGAMENT

[75] Inventor: Henk W. Wevers, Kingston, Canada

[73] Assignee: Queen's University at Kingston, Kingston, Canada

[21] Appl. No.: 972,997

[22] Filed: Dec. 26, 1978

[51] Int. Cl.³ .............................................. A61F 1/03
[52] U.S. Cl. ........................................... 3/1; 3/1.911; 128/92 B; 128/92 C; 128/92 D
[58] Field of Search ............................ 3/1, 1.9, 1.911; 128/92 D, 92 C, 92 B

[56] References Cited

U.S. PATENT DOCUMENTS

| | | | |
|---|---|---|---|
| 3,176,316 | 4/1965 | Bodell | 3/1 |
| 3,513,484 | 5/1970 | Hausner | 3/1 |
| 3,545,008 | 12/1970 | Bader, Jr. | 3/1 |
| 3,613,120 | 10/1971 | McFarland, Jr. | 3/1.91 |
| 3,797,047 | 3/1974 | Pillet | 3/1 |
| 3,805,300 | 4/1974 | Tascon-Alonso et al. | 3/1 |
| 3,896,500 | 7/1975 | Rambert et al. | 3/1 |
| 3,953,896 | 5/1976 | Treace | 3/1.9 X |
| 3,971,670 | 7/1976 | Homsy | 3/1 X |
| 3,973,277 | 8/1976 | Semple et al. | 3/1 |
| 4,149,277 | 4/1979 | Bokros | 3/1 |

Primary Examiner—Clifford D. Crowder
Attorney, Agent, or Firm—Richard J. Hicks; Stanley E. Johnson

[57] ABSTRACT

A prosthetic ligament device comprising an elastic element securable to the underlying bone structure by means of a quick release bayonet-type fitting which permits rotational movement during engagement at one end and a length adjusting means at the other end thereof. The elastic element comprises a plurality of parallel, longitudinal, polyester cords which form the warp, interwoven with a plurality of transverse soft silicone or polyurethane tubes which form the weft. Upon extension the soft tubes compress so as to permit a relatively large elongation of the elastic element at low stress, but upon continued extension the elastic element becomes progressively stiffer, simulating a natural ligament.

12 Claims, 16 Drawing Figures

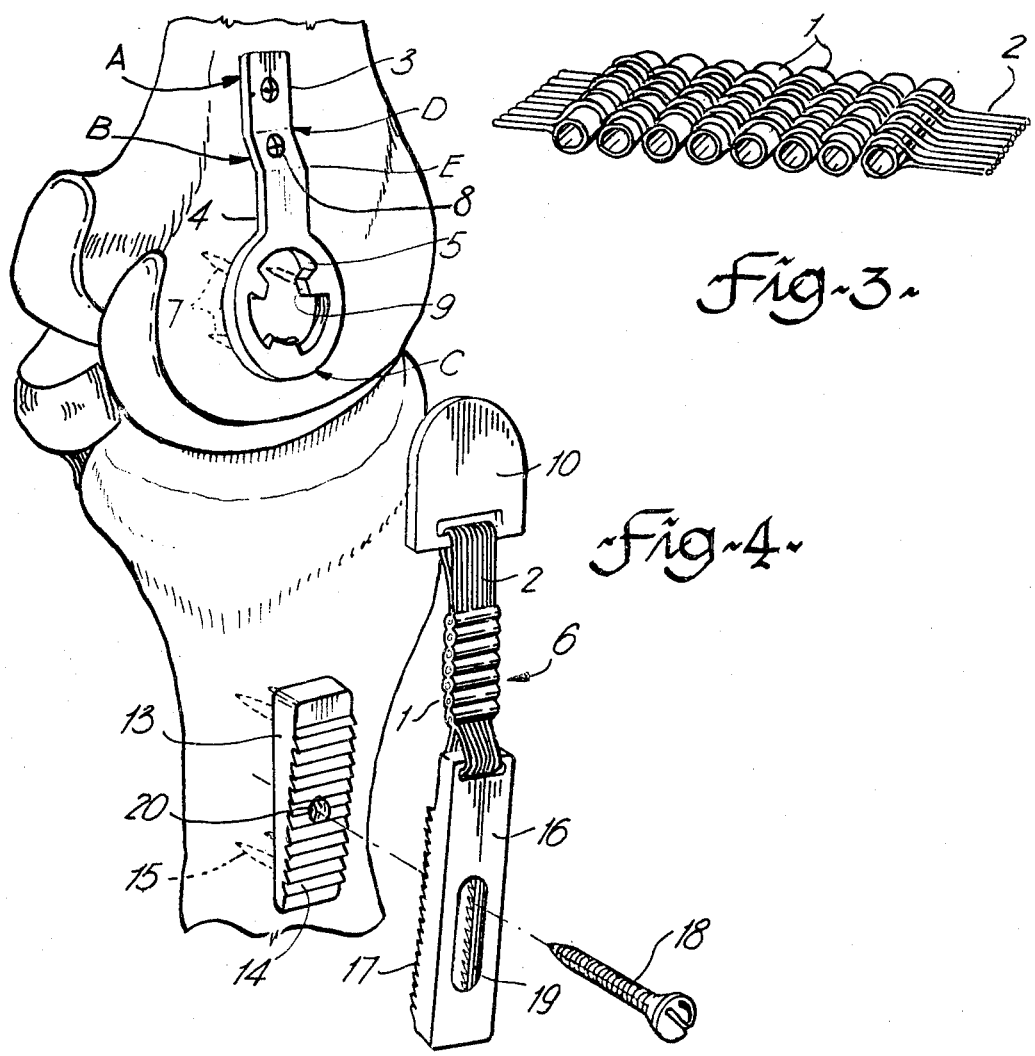
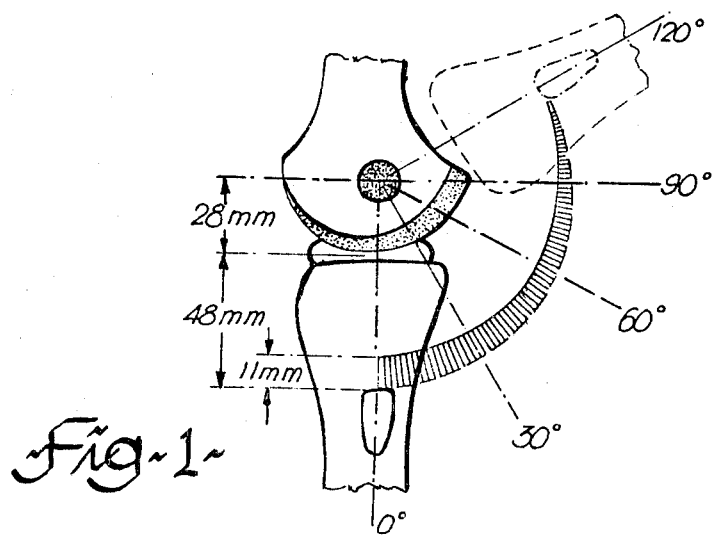

ARTIFICIAL LIGAMENT

This invention relates generally to prostheses and more specifically to prosthetic ligaments, particularly knee ligaments.

Ligaments are the tough, elastic, bandlike structures which bind the skeletal members together at the joints. Bending the knee, for example, sideways stretches the ligaments slightly. The force required to bend the knee, therefore, is related to the ability of the ligaments to resist stretching. Obviously, ligaments are frequently damaged when too great a force is applied as in a sports accident or the like, and ligaments are also frequently damaged by diseases such as rheumatoid arthritis. One ligament, in particular, is commonly involved in knee problems—the tibial collateral ligament which lies on the side of the joint towards the mid line and prevents the lower leg from bending outwards. While ligaments can often be repaired surgically, with little or no after effects, there are many cases where the damage or diseased tissue is too extensive for repair and resort must be had to some form of artificial ligament. Attempts have been made to replace the damaged ligament with other body tissue such as muscle or the like. However, such replacements tear in a short period of time as no other body tissue has the required combination of elastic and strength properties to act satisfactorily as a ligament. Other attempts have been made to provide artificial ligaments using man-made materials, such as those described in U.S. Pat. Nos. 3,953,896 Treace; 3,896,500 Rambert et al; 3,882,551 Helmer et al; 3,973,277 Semple et al and 3,545,008 Bader; and Canadian Pat. Nos. 937,702 Pillet; 977,902 Olowinski and 886,076 Medell. These attempts have all met with some success but there is still room for considerable improvement. All of the prior art devices suffer from one or more disadvantage, such as limited ligament life, difficulty of attachment to the bone and adjustment thereof once attached, and failure of the ligament structure to reproduce the peculiar elastic properties of a natural ligament. Heretofore artificial ligament structures have employed cords, elastomeric silicone materials, elastic fabrics, and ultra-high molecular weight polymers such as polyethylene, in a bio-compatible form. While such materials approximate a natural ligament, none of them alone can duplicate the elastic properties of a natural ligament. Using a Lowe Knee Analyser (Med. & Biol. Eng. & Comput., 1977, 15, 548–552) the deformation characteristics of the medial collateral ligament (MCL) have been determined accurately and it has been found that on initial movement of the knee there is a large elongation at a very low force, but in normal gait the MCL elongates approximately 3 mm and the force on the MCL is approximately 130N. At full extension the stiffness of the MCL is thus estimated at about 44N/mm at an average extension rate of 15 mm/min. This stiffness is approximately constant over the normal operating range in normal gait. Under emergency conditions however, the MCL must be able to withstand loads that are considerably higher than those occurring in normal gait. Loads of the order of 1000–1600N are not uncommon. The MCL should also become progressively stiffer as the load increases towards the ultimate load of the order of 1600N. Heretofore it has not been possible to provide an artificial ligament material having such variable and progressive stiffness characteristics. Further, anchoring and adjustment of artificial ligaments has caused considerable difficulty as the area available for a prosthetic base, adjacent the natural attachment point, is generally insufficient for a base large enough to withstand the tensile forces transmitted to the bone by the artificial ligament.

It is, therefore, an object of the present invention to provide a novel prosthetic ligament and means to operatively secure the same in position in a bone joint.

By one aspect of this invention there is provided a prosthetic ligament device for replacing a natural ligament flexibly connecting first and second natural skeletal members together, comprising:

(a) an elongated elastic element having elastic properties substantially similar to those of a natural ligament;

(b) lock means to releasably secure one end of said elastic element to said first skeletal member; and (c) means to secure the other end of said elastic element to said second skeletal member, including means to adjust said element to a predetermined length and stress level.

By another aspect of this invention there is provided a prosthetic ligament device for replacing a natural ligament flexibly connecting first and second natural skeletal members in a joint, comprising:

(a) a woven elastic element for joining the first and second skeletal members together, said elastic element having a plurality of parallel polyester cord warp elements interwoven with a plurality of parallel tube weft elements fabricated from a material selected from the group consisting of silicone and polyurethane;

(b) first and second bone anchor means for attachment to said first and second skeletal members respectively; and (c) connector means at each end of said polyester cords for releasable engagement with a respective one of said bone anchor means;

said first bone anchor means including means cooperating with its respective connector means to adjust said elastic element to a predetermined length and stress in said joint, and the said second anchor means including means to interlock with its respective connector means.

The invention will be described in more detail hereinafter with reference to the accompanying drawings in which:

FIG. 1 is a graphical representation of the extension of a medial collateral ligament as a function of knee flexion angle;

FIG. 4 is an isometric view of the prosthetic device of the present invention as applied as a medial collateral ligament of the left knee;

Turning firstly to FIG. 1, which represents graphically the extension of the medial collateral ligament (MCL) as a function of the knee flexion angle based on experiments conducted by Wang et al (J. Biol. Mech. 6, 587-596 (1973)), it is assumed that the MCL is not strained at 120° flexion. While it is not certain where exactly the MCL starts to strain when the knee rotates from 120° flexion to extension, it is believed reasonable to assume the MCL begins to exert a force prior to the extended position of the knee. As can be seen from FIG. 1, there is a relatively large extension, of the order of 11 mm from 120° flexion to the extended position, which has to be accommodated without exerting too much force. It is, of course, obvious that the mechanical properties of a prosthetic MCL should match those of a natural ligament as closely as possible, especially when the knee reaches the extended position and also in normal gait. The stiffness of the MCL is an important property that determines the force action, when strained, in maintaining mediolateral stability during normal gait. Using the Lowe Knee Analyser, supra, this mechanical behaviour of the ligament has been determined with some accuracy as the knee undergoes mediolateral bending, under controlled conditions at constant valgus and varus angular deflection rates, to a present moment limit. From these determinations the in vivo force-extension values of the MCL of healthy subjects can be estimated. At extension the stiffness of the MCL is estimated at about 44N/mm, at an average extension rate of 15 mm/min. These findings enable the establishment of the sloped dotted outer boundary starting from $l_1$ in the graph illustrated in FIG. 2. The distance between 0 and $l_1$ represents the elongation of the MCL between 120° flexion and extension of the knee joint.

Figure 2:
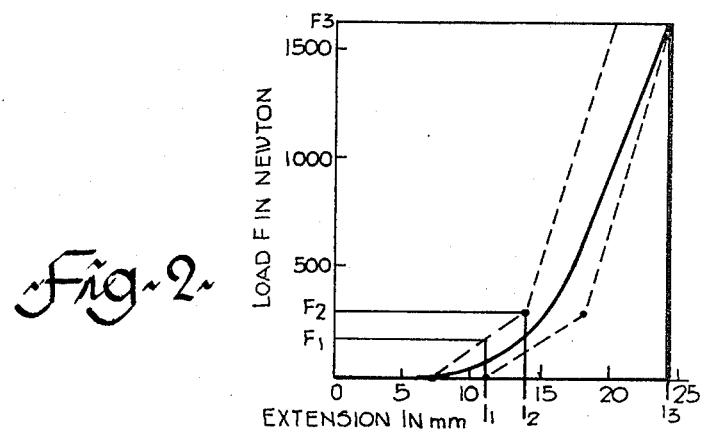
FIG. 2 is a graph illustrating an extension load curve for a prosthetic medial collateral ligament.

It has been previously determined (Morrison, J. Biomech. 3, 51-61 (1970)) that the force on the MCL in normal gait is about 130 N. When the in vivo stiffness as determined by the knee analyser, supra, is combined with Morrison's results, it can be calculated that in normal gait the MCL elongates about 3 mm. This elongation is represented in FIG. 2 by $l_1$–$l_2$ on the horizontal axis. The inner boundary in FIG. 2 may be established by shifting the dotted line representing a stiffness of 44 N/mm from $l_1$ to the left. This assumes the MCL will be strained to produce $F_1$, before the extended position of the knee is reached. Thus the prosthetic MCL should have operating properties, in normal gait, that fall in the region bounded by the vertical lines through $l_1$ and $l_2$ and the two dotted boundary lines in FIG. 2. It will be appreciated, of course, that the MCL must be able to withstand loads that are considerably higher than the loads occurring in normal gait. Using an Instron ® Tensile testing machine, and correcting for loss of strength due to the storage of cadaveric ligament in formaldehyde, it has been determined that the ultimate tensile strength of the MCL is of the order of 1600 N, which is represented by $F_3$ in FIG. 2. At the ultimate load, the elongation of cadaveric MCL is of the order of 24 mm, represented by $l_3$ in FIG. 2. Thus the two steeper dotted lines in FIG. 2 establish the desirable boundaries for ligament properties beyond normal gait. The solid line in FIG. 2 is an approximation of the most desirable properties for a prosthetic MCL, and it is to be noted that its slope is similar to that of a natural MCL as determined by other workers in this field (Crowinshield et al J. Biomech. 9, 397-405 (1976)).

It has been found difficult to employ metals in prosthetic MCLs because, although metals have easily predictable behaviour and properties, metal springs generally have poor overload characteristics and plastic deformation under overload conditions would render a prosthetic MCL useless. A combination of polyester cords and silicone rubber or soft polyurethane has, however, been found highly satisfactory. As seen most clearly in FIG. 3, a plurality of soft polyurethane (such as medical grade, manufactured by Ontario Research Foundation, Shore A hardness 40-60 ) or silicone rubber rods or, preferably, tubes 1 are placed in lateral side by side parallel relationship to form the weft, and a plurality, usually of the order of 10 of parallel polyester cords 2 are woven between adjacent tubes 1 to form the warp. A particularly suitable bio-compatible polyester cord is T777 provided by Canadian Celanese Company, which has a UTS of 40 lbs/cord (180 N) and 40% elongation at failure. This cord is made from 1000 Denier yarn (1000 gm/9000 meters) or a metric equivalent decitex no. of 1100 (1100 grams/10000 meters). The cord is 3-ply, i.e. 3 individual yarns twisted together with 8 twists/inch (320 twists/meter). The filaments making up the individual yarns are twisted together with 13.5 twists per inch (540 twists/meter) in the opposite direction. The cords are heat treated and coated with a biocompatible abrasion resistant polyurethane (medical grade by O. R. F. Shore A hardness 40-60). The elastic elongation of 40% at the ultimate load of 180 N is particularly advantageous in accidental overloading of the MCL and it will be appreciated that the load-extension properties of the cords can be readily controlled by varying the number of twists/length unit and by the number of filaments in the cord.

Figure 3:
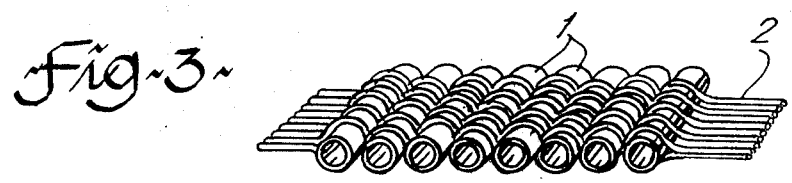
FIG. 3 is an isometric sketch of a prosthetic ligament material contemplated by the present invention.

When the elastic element, shown in FIG. 3, is extended it will exhibit an initial large extension at low force as the silicone tubes are squeezed by the cords and tend to flatten and become solid. This initial stage corresponds to the 0–$l_1$ extension of FIG. 2. As the tubes flatten there is an exchange between the tubes and the cords which take over the elastic loading. The elastic element rapidly stiffens in the region of normal gait ($l_1$–$l_2$) and it becomes relatively very stiff at larger extensions. It will be appreciated that by varying the diameter and the number of silicone tubes 1 in the weft, the desired curve of FIG. 2 can be matched. Similarly, desired properties and specific characteristics for other substitute or prosthetic ligaments can also be obtained.

It is usually desirable to sheathe the elastic element of FIG. 3 with a biocompatible wear layer of soft polyurethane, such as the medical grade developed by the Ontario Research Foundation supra. Both the weft and warp are normally coated so as to provide a compact and unitary structure which affords minimal surface area and hence is less subject to wear or interference by physiological functions.

Following production of a suitable elastic element the properties of which can be selected to match those of selected natural ligament, there remains the problem of attaching or implanting the elastic element to the underlying bone structure. Taking the MCL, for example, it will be appreciated that a capability for minor length adjustment of the elastic element is of considerable assistance to the orthopedic surgeon. It has been found convenient to provide the length adjustment on the tibial attachment. As long term wear of the cords at the femoral and tibial attachment points is inevitable, although it can be reduced by correct balance of the polyurethane coating and good design of the anchors, it is most desirable that the elastic element should be relatively easily replaceable. Although a surgical operation is obviously required to effect replacement, such an operation can be simplified if only a standard elastic element has to be replaced, and for this reason a quick release fitting at the femoral and tibial ends is preferred.

Figure 5:
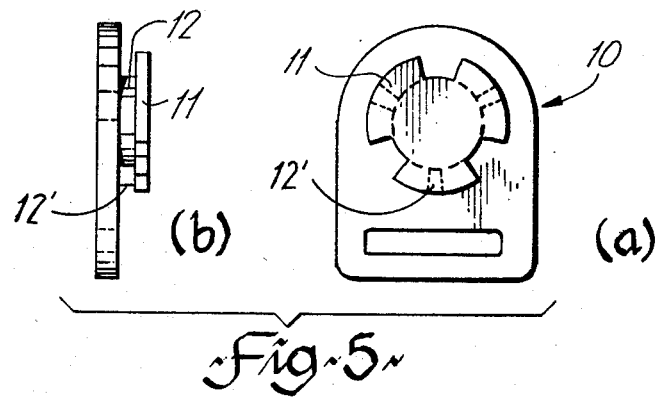
FIGS. 5a and 5b are front and side views respectively of the bayonet fitting for the femoral attachment element of the prosthetic device shown in FIG. 4.

The natural femoral attachment of the MCL consists of collagen fibre growing into the porous bone of the femur. The area available for a prosthetic base is approximately 15-20 mm in diameter, which is insufficient to withstand the tensile force that the substitute MCL transmits to the bone. One solution to this problem is to extend an arm 3 of the prosthesis base plate 4 proximally up the femur shaft as shown more clearly in FIG. 4. The base plate 4 and arm 3 are preferably fabricated from a cobalt-chrome alloy, sold commercially under trade names such as Vitallium ® or Inertia ®, which has been found to be strong and biocompatible. The bayonet type fitting or receptacle 5 for the femoral connection of the elastic element assembly 6 is anchored in the spongy bone at the natural ligament attachment site by means of a plurality of bone pins 7, preferably arranged as a tripod. The main tensile force exerted by the substitute MCL is thus transmitted from the pins 7 through the arm 3 to one or more bone screws 8 in the harder cortical bone of the femur. Preferably, a porous metal coating is applied to the prosthesis at points A, B and C and on pins 7 which will stimulate bone ingrowth which, in turn, will promote the formation of a firm attachment. The arm 3 is designed to be bent at points D and E during surgery to match the anatomical shape of the medial side of the femur which will produce firm contact between prosthesis and bone at the points which are porous metal coated. The bayonet fitting 5 is, in the preferred embodiment shown in FIG. 4, substantially circular and provided with radially inwardly directed lugs 9, and adapted to slidingly receive a complementary shaped connector 10, secured to the femoral end of the cords 2, of the elastic element assembly 6. Connector 10 is provided with a complementary shaped button 11, shown more clearly in FIG. 5, on a circular shank 12, for axial movement and limited rotation, relative to lugs 9 in bayonet fitting 5 between an insertion position and a locked operational position in which stops 12' engage lugs 9 to provide for easy and rapid assembly and/or replacement of the elastic element.

The natural tibial attachment of the MCL is an area of the tibia approximately 15×25 mm, and there is ample space on the tibia to attach a tibial base plate for attachment of the substitute MCL. In a preferred embodiment, shown in FIG. 4, the tibial base plate 13 is a substantially rectangularly shaped wedge having a toothed upper surface 14. A plurality of pins 15 are adapted for insertion into predrilled holes in the tibia for stability during surgery and during the first stages of bone ingrowth. The base plate 13 is fabricated in Vitallium ® or Inertia ® as previously described and the base and the pins are preferably porous metal coated in order to promote bone ingrowth. The elastic element assembly 6 is provided with a complementary rectangular shaped wedge plate 16 having a complementary toothed surface 17 for releasable and adjustable engagement with toothed surface 14 of base plate 13. During surgery the toothed surfaces 14 and 17 are engaged and moved relative to each other so as to adjust the length of the elastic element 6 to a precisely determined length. When the desired length and degree of pre-stretching is achieved the plates 13 and 16 are locked together by means of a screw 18, passing through a slot 19 in plate 16 and hole 20 in plate 13, and anchored in the tibia. The screw 18 secures the plate 16 on plate 13 without itself being subjected to an appreciable lateral force.

It will be appreciated that, although this specification has thus far stressed the medical collateral ligament, the principles of the present invention may be applied to the provision of many other substitute ligaments. Similarly, there are many variations in the manner of attachment of the elastic element to the underlying bone structure, some of which will be described hereinafter with reference to FIGS. 6-9.

Figure 9:
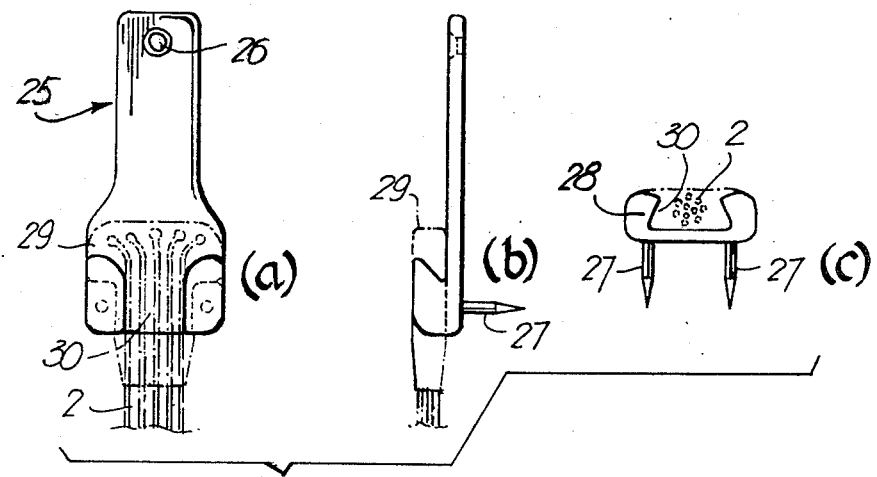
FIGS. 9a, 9b and 9c are plan, side and end views respectively of an alternative femoral attachment for use in the present invention.
Figure 6:
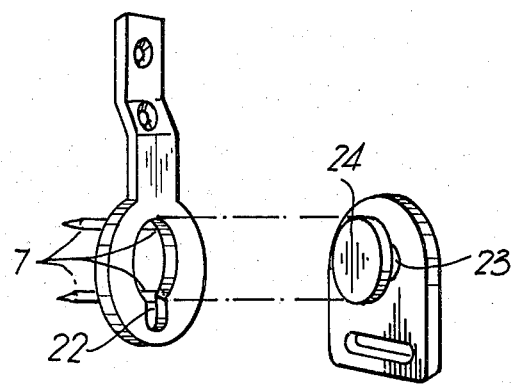
FIG. 6 is a sketch of an alternative femoral attachment element for use in the prosthetic device of the present invention.

In FIG. 6 there is shown an alternative femoral end attachment similar in general outline to the attachment plate 3 described above, but having a single elongated lock slot 22 shaped to receive a complimentary shaped shank 23 of the attachment button 24 for locking engagement therewith. In FIG. 9 there is shown another alternative femoral end attachment plate 25, similar in outline shape to those previously described, provided with a bone screw hole 26 and and a plurality of bone pins 27. The anchor for the elastic element 6 is, however, rather different and comprises a tapered, rabbeted slot 28 into which the shank 30 of a T-shaped end piece 29, preferably a heavy duty polyethylene or polyurethane moulding, is designed to be releasably wedged. Cords 2 of elastic element 6 are moulded into end piece 29.

Figure 7:
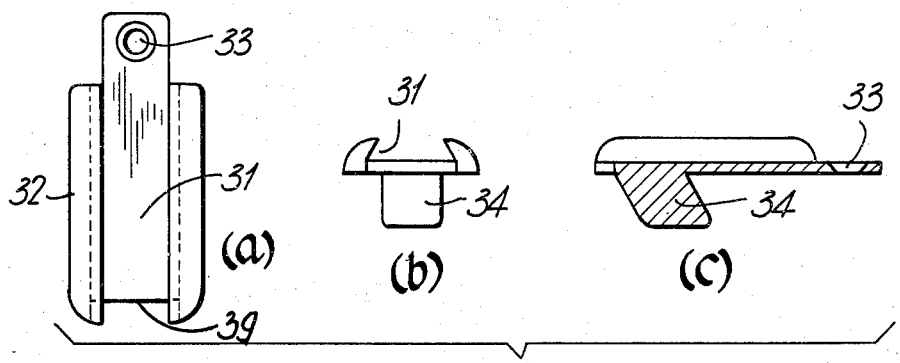
FIGS. 7a, 7b and 7c are plan, end and sectional views respectively of an alternative tibial bone attachment element for use in the prosthetic device illustrated in FIG. 3.
Figure 8:
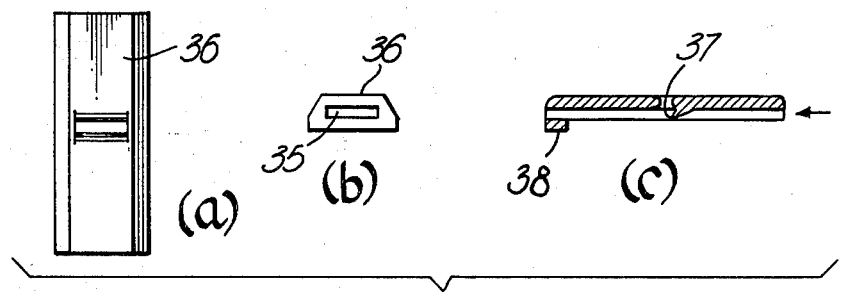
FIGS. 8a, 8b and 8c are plan, end and sectional views respectively of an insert for use with the tibial attachment element shown in FIG. 7.

In FIG. 7 there is shown an alternative tibial end attachment, similar in concept to the femoral attachment described with reference to FIG. 9. A rabbeted slot 31 is provided in tibial attachment plate 32 to receive and releasably engage a shaped high density polyethylene insert 36 shown in FIG. 8 into which in turn cords 2 of an elastic element 6 can be inserted. Plate 32 is provided with a bone screw hole 33 and an angled anchor block 34 designed for insertion into a recess cut into the tibia. FIG. 8b shows an end view of the insert 36 having shaped sides which mate with rabbeted slot 31. Insert 36 is provided with a shear tab 38 (FIG. 8c) which engages end 39 (FIG. 7a) to provide an overload shear device. Insert 36 is also provided with a toothed projection 37 depending from the top surface thereof, to engage with a high density polyethylene serrated strip moulded over the ends of cords 2 of an elastic element 6.

I claim:

1. A prosthetic ligament device for replacing a natural ligament flexibly connecting first and second natural skeletal members together, comprising:
   (a) an elongated elastic element having elastic properties substantially similar to those of a natural ligament and comprising a plurality of interwoven parallel cord wrap elements and parallel transverse radially deformable tubular weft elements;
   (b) lock means to releasably secure one end of said elastic element to said first skeletal member; and
   (c) means to secure the other end of said elastic element to said second skeletal member, including means to adjust said element to a predetermined length and stress level.

2. A prosthetic ligament device as claimed in claim 1 wherein the warp element comprises a plurality of substantially parallel longitudinal polyester cords.

3. A prosthetic ligament device as claimed in 1 wherein said deformable tubular elements are fabricated from a material selected from the group consisting of a medical grade soft polyurethane and silicone rubber.

4. A prosthetic ligament device as claimed in claim 3 wherein said warp and weft elements are coated with a biocompatible material so as to produce a unitary wear resistant structure.

5. A prosthetic ligament device for replacing a natural ligament flexibly connecting first and second natural skeletal members in a joint, comprising:
   (a) a woven elastic element for joining the first and second skeletal members together, said elastic element having a plurality of parallel polyester cord warp elements interwoven with a plurality of parallel tube weft elements fabricated from a material selected from the group consisting of silicone and polyurethane;
   (b) first and second bone anchor means for attachment to said first and second skeletal member respectively; and
   (c) connector means at each end of said polyester cords for releasable engagement with a respective one of said bone anchor means;
said first bone anchor means including means cooperating with its respective connector means to adjust said elastic element to a predetermined length and stress in said joint, and the said second anchor means including means to interlock with its respective connector means.

6. A prosthetic ligament device as claimed in claim 5 wherein said first anchor means comprises a plate having a toothed surface for releasable and adjustable engagement with a complementary toothed surface on the respective connector means; and including means to releasably secure said first anchor means and its respective connector means in a selected overlying relationship.

7. A prosthetic ligament device as claimed in claim 6 wherein said second anchor means comprises a ring means to receive and releasably engage a complementary shank means on its respective connector means.

8. A prosthetic ligament device as claimed in claim 7 wherein said ring means includes radially inwardly projecting lug means and the respective connector means includes button means for releasable engagement with said lug means.

9. A prosthetic ligament device as claimed in claim 7 wherein said ring means includes a radially outwardly extending slot means for engagement with said shank means, and the respective connector means includes button means for insertion through said ring means.

10. A prosthetic ligament device as claimed in claim 7 wherein said second anchor means includes an arm extending from said ring means along said second skeletal member and away from said joint.

11. A prosthetic ligament device as claimed in claim 5 wherein surfaces of said first and second bone anchor means adjacent said skeletal members are coated with a porous metal coating so as to promote bone ingrowth.

12. A prosthetic ligament device as claimed in claim 11 wherein said first and second bone anchor means include bone pins for insertion in predrilled holes in said skeletal members.

* * * * *